(12) United States Patent
Yang et al.

(10) Patent No.: US 9,705,094 B2
(45) Date of Patent: Jul. 11, 2017

(54) ORGANIC SEMICONDUCTOR COMPOUND, ORGANIC THIN FILM INCLUDING SAME, AND ELECTRONIC DEVICE INCLUDING THE ORGANIC THIN FILM

(71) Applicant: Samsung Electronics Co., Ltd., Suwon-si, Gyeonggi-do (KR)

(72) Inventors: Hyeyeon Yang, Yongin-si (KR);
Youngjun Yun, Seongnam-si (KR);
Suk Gyu Hahm, Gyungju-si (KR);
Jeong Il Park, Seongnam-si (KR);
Jong Won Chung, Hwaseong-si (KR);
Sang Yoon Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/950,294

(22) Filed: Nov. 24, 2015

(65) Prior Publication Data
US 2016/0149143 A1    May 26, 2016

(30) Foreign Application Priority Data

Nov. 26, 2014  (KR) ........................ 10-2014-0166827

(51) Int. Cl.
*C07D 487/04*   (2006.01)
*H01L 51/00*    (2006.01)
*H01L 51/05*    (2006.01)

(52) U.S. Cl.
CPC ........ *H01L 51/0072* (2013.01); *C07D 487/04* (2013.01); *H01L 51/0545* (2013.01); *H01L 51/0558* (2013.01)

(58) Field of Classification Search
CPC .......................... H01L 51/0072; C07D 487/04
See application file for complete search history.

(56) References Cited

U.S. PATENT DOCUMENTS

| 9,169,206 B2 | 10/2015 | Han et al. |
| 2011/0031484 A1 | 2/2011 | Lee et al. |
| 2013/0207082 A1 | 8/2013 | Cho et al. |

FOREIGN PATENT DOCUMENTS

| EP | 2629346 A2 | 8/2013 |
| KR | 20110041726 A | 4/2011 |
| KR | 20130073700 A | 7/2013 |
| WO | WO-2010/074520 A2 | 7/2010 |
| WO | WO-2010/110553 A2 | 9/2010 |
| WO | WO-2010/126234 A1 | 11/2010 |

OTHER PUBLICATIONS

Takemura, et al. Document No. 148:133674 for JP 2008010541; Jan. 17, 2008; retrieved from STN.*
Heilbronner, et al. "Prediction of the spectra of aromatic hydrocarbons" Journal of the Chemical Society, pp. 2611-26115 (1962).
Zander, et al. "Carbazolocarbazoles", Chemische Berichte, vol. 102(8), pp. 2728-2738 (1969).
Mas-Montoya, et al. "Isomeric carbazolocarbazoles: synthesis, characterization and comparative study in Organic Field Effect Transistors", Journal of Materials C: Materials for Optical and Electronic Devices, vol. 1 (10), pp. 1959-1969 (2013).

* cited by examiner

*Primary Examiner* — Shawquia Jackson
(74) *Attorney, Agent, or Firm* — Harness, Dickey & Pierce, P.L.C.

(57) ABSTRACT

An organic semiconductor compound represented by Chemical Formula 1 is highly fused due to fusion of greater than or equal to 4 rings, and has smooth intermolecular charge transfer due to relatively high planarity.

10 Claims, 3 Drawing Sheets

ORGANIC SEMICONDUCTOR COMPOUND, ORGANIC THIN FILM INCLUDING SAME, AND ELECTRONIC DEVICE INCLUDING THE ORGANIC THIN FILM

CROSS REFERENCE TO RELATED APPLICATIONS

This application claims priority to and the benefit of Korean Patent Application No. 10-2014-0166827 filed in the Korean Intellectual Property Office on Nov. 26, 2014, the entire contents of which are incorporated herein by reference.

BACKGROUND

1. Field

Example embodiments relate to an organic semiconductor compound, an organic thin film including the same, and an electronic device including the organic thin film.

2. Description of the Related Art

In general, flat display devices, e.g., liquid crystal displays or organic electroluminescent displays, are provided with a variety of thin film transistors (TFTs) to drive the devices. The TFT may include a gate electrode, source/drain electrodes, and a semiconductor layer that may be activated in response to operation of the gate electrode. The semiconductor layer may include an organic semiconductor material that is controlled by a current between the source electrode and the drain electrode using an applied gate voltage.

Recently, research on a polymer organic material such as polythiophene or a low molecular organic material such as pentacene as an organic semiconductor material used for a channel of a thin film transistor have been made. However, the polymer organic material has relatively low charge mobility but a relatively high blocking leakage current. On the other hand, the relatively low molecular organic material such as pentacene, etc. is reported to have relatively high charge mobility of greater than or equal to about 3.2 to about 5.0 cm$^2$/Vs, but needs expensive vacuum deposition equipment to form a thin film, and thus may not be appropriate in terms of processibility and formation of a large area.

Accordingly, development of a new organic semiconductor material simultaneously having improved electrical characteristics and desirable processibility is continuously required.

SUMMARY

Example embodiments provide an organic semiconductor compound that performs intermolecular packing and stacking to have relatively high charge mobility due to a compact planar structure.

Example embodiments also provide an organic thin film including the organic semiconductor compound.

Example embodiments also provide an electronic device including the thin film, thereby having improved electrical characteristics.

According to example embodiments, an organic semiconductor compound is represented by Chemical Formula 1.

[Chemical Formula 1]

In Chemical Formula 1,
each of $R^1$ and $R^2$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, and a substituted or unsubstituted $C_2$ to $C_{30}$ alkynyl group,
each of $R^3$ to $R^8$ are independently one of hydrogen, a substituted or unsubstituted $C_1$ to $C_{10}$ alkyl group, and a substituted or unsubstituted $C_1$ to $C_{10}$ alkoxy group,
each of n1 and n2 are independently one of 0 to 2,
m is 0 or 1,
each of a and f are independently one of 0 to 4, and
each of b, c, d, and e are independently one of 0 to 2.
One example of the $R^1$ and $R^2$ may be one of a substituted or unsubstituted $C_{10}$ to $C_{30}$ alkyl group, a substituted or unsubstituted $C_{10}$ to $C_{30}$ alkoxy group, a substituted or unsubstituted $C_{10}$ to $C_{30}$ alkenyl group, and a substituted or unsubstituted $C_{10}$ to $C_{30}$ alkynyl group, and another example may be a fluoro substituted $C_1$ to $C_{30}$ alkyl group, for example, one of a $C_1$ to $C_{30}$ perfluoro alkyl group ($C_nF_{2n+1}$, wherein n is an integer of 1 or more) and a fluoro substituted $C_{10}$ to $C_{30}$ alkyl group, or a $C_{10}$ to $C_{30}$ perfluoro alkyl group ($C_nF_{2n+1}$, wherein n is an integer of 1 or more).

The organic semiconductor compound may be one of organic semiconductor compounds represented by Chemical Formulae 1A to 1H.

[Chemical Formula 1A]

[Chemical Formula 1B]

[Chemical Formula 1C]

-continued

[Chemical Formula 1D]

[Chemical Formula 1E]

[Chemical Formula 1F]

[Chemical Formula 1G]

[Chemical Formula 1H]

In the Chemical Formulae 1A to 1H, each of $R^1$ and $R^2$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, and a substituted or unsubstituted $C_2$ to $C_{30}$ alkynyl group, each of $R^3$ to $R^8$ are independently one of hydrogen, a substituted or unsubstituted $C_1$ to $C_{10}$ alkyl group, and a substituted or unsubstituted $C_1$ to $C_{10}$ alkoxy group, each of a and f are independently one of 0 to 4, and each of b, c, d, and e are independently one of 0 to 2.

The organic semiconductor compound may have an average molecular weight of about 350 to about 3,000.

According to example embodiments, an organic thin film includes the organic semiconductor compound.

According to example embodiments, an electronic device includes the organic semiconductor compound.

The electronic device may be one of a transistor, an organic light emitting diode (OLED), a photovoltaic device, a solar cell, a laser device, a memory device, and a sensor.

The electronic device may include at least one charge transport layer, and the organic semiconductor compound may be included in the charge transport layer.

DETAILED DESCRIPTION

The present disclosure will be described more fully hereinafter with reference to the accompanying drawings, in which example embodiments of this disclosure are shown. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, the term "combination thereof" refers to a mixture, a stacked structure, etc.

Hereinafter, as used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

The term "alkenyl group" may refer to a linear or branched saturated monovalent hydrocarbon group including at least one carbon-carbon double bond (e.g., an ethenyl group).

The term "alkynyl group" may refer to a linear or branched saturated monovalent hydrocarbon group including at least one carbon-carbon triple bond (e.g., ethynyl group).

The term "alkoxy group" may refer to an alkyl group that is linked via an oxygen, e.g., a methoxy, an ethoxy, and a sec-butyloxy group.

As used herein, when a definition is not otherwise provided, the term "substituted" means that a functional group or a compound is substituted with at least one substituent selected independently from a halogen (—F, —Cl, —Br, or —I), a $C_1$ to $C_{10}$ linear or branched alkyl group, a $C_2$ to $C_{10}$ linear or branched alkenyl group, a $C_2$ to $C_{10}$ linear or branched alkynyl group, a $C_1$ to $C_{10}$ fluoroalkyl group, a $C_1$ to $C_{10}$ perfluoroalkyl group ($C_nF_{2n+1}$), a $C_1$ to $C_{10}$ linear or branched alkoxy group, provided that the normal valence of the substituted atom is not exceeded.

Hereinafter, an organic semiconductor compound according to example embodiments is described.

According to example embodiments, an organic semiconductor compound represented by Chemical Formula 1 is provided.

[Chemical Formula 1]

In Chemical Formula 1, each of $R^1$ and $R^2$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, and a substituted or unsubstituted $C_2$ to $C_{30}$ alkynyl group, each of $R^3$ to $R^8$ are independently one of hydrogen, a substituted or unsubstituted $C_1$ to $C_{10}$ alkyl group, and a substituted or unsubstituted $C_1$ to $C_{10}$ alkoxy group, each of n1 and n2 are independently one of 0, 1 and 2, m is 0 or 1, and each of a to f are independently integers corresponding to the number of aromatic rings, for example, each of a and f are independently one of 0 to 4, and each of b, c, d, and e are independently one of 0 to 2.

The organic semiconductor compound has a basic structure of carbazolo[4,3-c]carbazole formed through fusion of two carbazoles. The structure formed by the fusion in this direction may maximize or increase planarity of the organic semiconductor compound and overlap of an intermolecular orbital and thus improve charge mobility.

In the organic semiconductor compound, substituents such as $R^1$ and $R^2$ are relatively easy to introduce into the carbazole structure. One example of the $R^1$ and $R^2$ may be a substituted or unsubstituted $C_{10}$ to $C_{30}$ alkyl group or a substituted or unsubstituted $C_{10}$ to $C_{30}$ alkoxy group, and another example may be a fluoro substituted $C_1$ to $C_{30}$ alkyl group, for example, a $C_1$ to $C_{30}$ perfluoro alkyl group or a fluoro substituted $C_{10}$ to $C_{30}$ alkyl group, or a $C_{10}$ to $C_{30}$ perfluoro alkyl group. The introduction of the substituent may increase intermolecular interaction, and thus the organic semiconductor compound may have a desirable molecular arrangement, improving charge mobility. In addition, the introduction of the substituent may improve dissolution of the organic semiconductor compound and facilitate its synthesis, and thus its mass production. Accordingly, a solution process for forming a thin film may be more easily performed.

When a substituent having a ring structure such as an aryl group or a cycloalkyl group is introduced as the $R^1$ and $R^2$ substituents, the molecules of the organic semiconductor compound are not easily arranged, reducing mobility.

Each of the a to f are independently integers corresponding to the number of aromatic rings, for example, a and f may be 0 to 4, and b, c, d, and e may be 0 to 2. When a to f are 2 or more, each $R^3$ to $R^8$ may be the same as or different from each other.

The organic semiconductor compound has a compact planar structure where 4 or more rings are fused to each other, and intermolecular stacking may be well realized and a conjugation structure may be well formed to have improved charge mobility.

The organic semiconductor compound may be one of organic semiconductor compounds represented by Chemical Formulae 1A to 1H.

[Chemical Formula 1A]

[Chemical Formula 1B]

[Chemical Formula 1C]

[Chemical Formula 1D]

[Chemical Formula 1E]

[Chemical Formula 1F]

[Chemical Formula 1G]

[Chemical Formula 1H]

In the Chemical Formulae 1A to 1H, each of $R^1$ and $R^2$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, and a substituted or unsubstituted $C_2$ to $C_{30}$ alkynyl group, each of $R^3$ to $R^8$ are independently one of hydrogen, a substituted or unsubstituted $C_1$ to $C_{10}$ alkyl group, and a substituted or unsubstituted $C_1$ to $C_{10}$ alkoxy group, and each of a to f are independently integers corresponding to the number of aromatic rings, for example, each of a and f are independently one of 0 to 4, and each of b, c, d, and e are independently one of 0 to 2.

In the Chemical Formulae 1A to 1H, $R^1$, $R^2$, $R^3$ to $R^8$, and a to f are the same as described in Chemical Formula 1.

The organic semiconductor compound according to example embodiments may have an average molecular weight of about 350 to about 3000. When the organic semiconductor compound has the average molecular weight within the range, the organic semiconductor compound may be more easily handled.

Specific examples of the organic semiconductor compound may be compounds (1) to (14).

(1)

(2)

(3)

The HOMO energy, reorganization energy, and expectation mobility of compounds (1) to (6) of the compounds (1) to (14) are calculated, and the results are shown in Table 1. The HOMO energy and reorganization energy are calculated by using the Gaussian 03 program in DFT B3PW91 6-311G+ (d, p) level, transfer integrals are calculated by using ADF (the Amsterdam Density Functional) program in PW91-TZP, and then the expectation mobility is calculated according to a Marcus theory. For comparison, the HOMO energy, reorganization energy, and expectation mobility of compounds ref-1 and ref-2 are also shown in Table 1.

Ref-1 ref-2

TABLE 1

| Compound | $E_{HOMO}$ (eV) | Reorganization Energy (eV) | Expectation mobility (cm$^2$/Vs) |
|---|---|---|---|
| compound ref-1 | −4.61 | 0.218 | 1.25 |
| compound ref-2 | −5.59 | 0.218 | 0.142 |
| compound (1) | −5.04 | 0.190 | 0.358 |
| compound (2) | −4.84 | 0.215 | 0.212 |
| compound (3) | −4.84 | 0.214 | 0.210 |
| compound (4) | −4.84 | 0.214 | 0.209 |
| compound (5) | −4.85 | 0.0968 | 0.331 |
| compound (6) | −4.65 | 0.116 | 0.250 |

As shown in Table 1, the compounds (1) to (6) are expected to have improved intermolecular charge transfer compared with the compounds ref-1 and ref-2 since the compounds (1) to (6) have smaller reorganization energy than the compounds ref-1 and ref-2. The expectation mobility of the compounds (1) to (6) show larger expectation mobility than compounds ref-1 and ref-2.

The organic semiconductor compound is an N-containing condensed polycyclic aromatic compound included 4 or more rings fused to each other, and an organic thin film including the same may be applied to a carrier transport layer of an electronic device.

The organic semiconductor compound may provide an electronic device having improved electrical characteristics.

Example embodiments provide an organic thin film including the organic semiconductor compound and an electronic device including the organic thin film.

The organic thin film according to example embodiments includes the organic semiconductor compound, and thus may be used as an organic semiconductor layer for an electronic device and a carrier transport layer such as a channel layer, and the electronic device including the organic thin film shows improved electrical characteristics with relatively high charge mobility as well as desirable processibility and workability.

Herein, the organic thin film may be manufactured by depositing more than one kind of the organic semiconductor compound on a substrate in a common method or dissolving it in an organic solvent and coating the solution in a common room temperature solution process, and the deposited or coated thin film may be heat-treated to increase density and uniformity thereof.

Particularly, the organic solvent may include at least one kind of general organic solvent, for example, at least one kind of an aliphatic hydrocarbon solvent such as hexane, heptane, etc.; an aromatic hydrocarbon solvent such as toluene, pyridine, quinoline, anisole, mesitylene, xylene, etc.; a ketone-based solvent such as methyl isobutyl ketone, 1-methyl-2-pyrrolidinone, cyclohexanone, acetone, etc.; an ether-based solvent such as tetrahydrofuran, isopropyl ether, etc.; an acetate-based solvent such as ethyl acetate, butyl acetate, propylene glycol methyl ether acetate, etc.; an alcohol-based solvent such as isopropyl alcohol, butanol, etc.; an amide-based solvent such as dimethyl acetamide, dimethyl formamide, etc.; a silicone-based solvent; and a mixture of the solvents. The amount of the organic semiconductor compound dissolved in the organic solvent may be appropriately selected and determined by a person of ordinary skill in the art, for example, in a range of about 0.01 wt % to about 50 wt % in the total solvent in view of solubility and coating property.

The method of providing an organic thin film may include thermal deposition, vacuum deposition, laser deposition, screen printing, printing, imprinting, spin casting, dipping, ink jetting, roll coating, flow coating, drop casting, spray coating, roll printing, etc., but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, and is in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory device, a sensor, etc., and the organic thin film may be applied to each device according to the general process commonly known in the art.

For example, the transistor includes a gate electrode disposed on a substrate, a source electrode and a drain electrode facing each other and defining a channel region, an insulation layer electrically insulating the source electrode and drain electrode and the gate electrode, and an active layer including the organic semiconductor compound formed in the channel region.

The active layer may be obtained by depositing the fused polycyclic heteroaromatic compound, or applying a composition including the organic semiconductor compound to a solution process such as screen printing, printing, spin coating, dipping, ink jetting, etc. When the active layer is formed by the solution process, the process cost may be reduced, and a relatively wide area device may be effectively manufactured.

Figure 1:
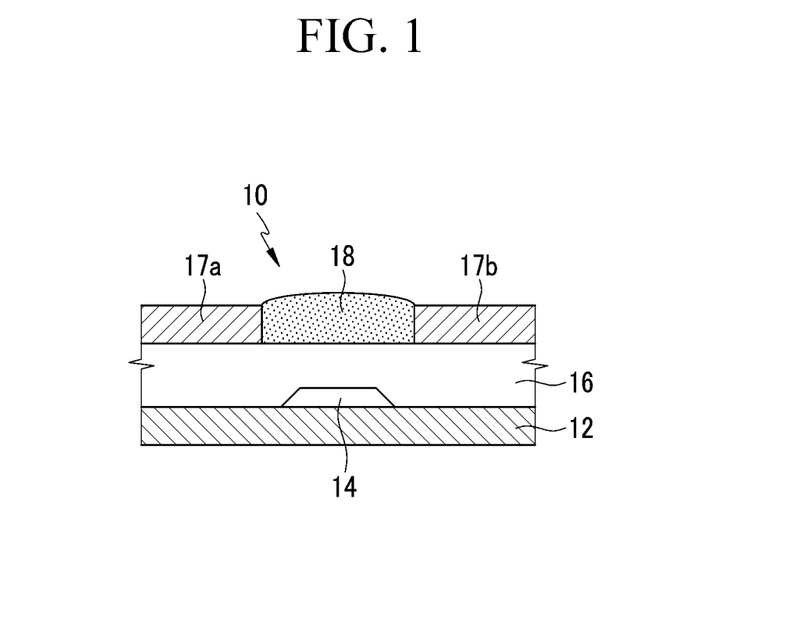
FIG. 1 is a schematic cross-sectional view showing a transistor according to example embodiments.
Figure 2:
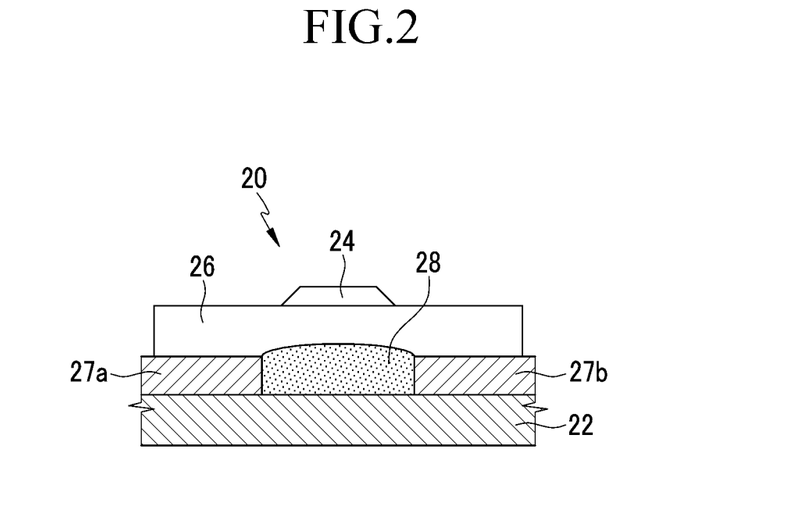
FIG. 2 is a schematic cross-sectional view showing a transistor according to example embodiments.

FIGS. 1 and 2 are schematic cross-sectional views showing a transistor according to example embodiments of the inventive concepts. The transistor according to example embodiments of the inventive concepts may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the organic semiconductor compound.

Referring to FIG. 2, a transistor 20 includes a source electrode 27a and a drain electrode 27b defining a channel region and that are formed on a substrate 22, and an active layer 28 formed on the channel region. The active layer 28 includes the organic semiconductor compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic such as polyethylene naphthalate (PEN), polyethylene terephthalate (PET), polycarbonate, polyvinyl alcohol, polyacrylate, polyimide, polynorbornene, and polyethersulfone (PES), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but are not limited thereto.

The insulation layers 16 and 26 may include a generally-used insulator having a high dielectric constant, particularly a ferroelectric insulator such as $Ba_{0.33}Sr_{0.66}TiO_3$ (BST, barium strontium titanate), Al$_2$O$_3$, Ta$_2$O$_5$, La$_2$O$_5$, Y$_2$O$_3$, and TiO$_2$; an inorganic insulator such as PbZr$_{0.33}$Ti$_{0.66}$O$_3$ (PZT), Bi$_4$Ti$_3$O$_{12}$, BaMgF$_4$, SrBi$_2$(TaNb)$_2$O$_9$, Ba(ZrTi)O$_3$ (BZT), BaTiO$_3$, SrTiO$_3$, SiO$_2$, SiN$_x$ (x is determined depending on valence of Si), AlON (aluminum oxynitride), etc.; or an organic insulator such as polyimide, benzocyclobutane (BCB), parylene, polyacrylate, polyvinyl alcohol, polyvinylphenol, etc., but are not limited thereto. Although it is not mentioned above, the inorganic insulator disclosed in U.S. Pat. No. 5,946,551 and the organic insulator disclosed in U.S. Pat. No. 6,232,157 may be used for the insulation layers 16 and 26.

Hereinafter, the present disclosure is illustrated in more detail with reference to examples. However, these are examples, and the present disclosure is not limited thereto.

SYNTHESIS OF ORGANIC SEMICONDUCTOR COMPOUND

Example 1: Synthesis of Organic Semiconductor Compound (1)

The organic semiconductor compound (1) is synthesized according to Reaction Scheme 1 by using a method described in Synlett, 2006, 7, 1021 and J. Heterocycl. Chem. 2007, 44, 161.

[Reaction Scheme 1]

(1)

$^1$H-NMR (CDI$_3$, 300 MHz) d 12.18 (s, 2H), 8.36 (d, 2H), 8.27 (d, 2H), 8.22 (d, 2H), 7.67 (d, 2H), 7.44 (d, 2H), 7.26 (d, 2H).

$^{13}$C-NMR (CDCl$_3$, 75 MHz) d 141.3, 138.5, 123.3, 121.4, 120.0, 119.8, 118.8, 115.3, 111.1, 103.0.

Example 2: Synthesis of Organic Semiconductor Compound (2)

The organic semiconductor compound (2) is synthesized according to Reaction Scheme 2. First, the organic semiconductor compound (1) of Example 1 (3 g, 9.8 mmol) is dissolved in 200 mL of dimethyl sulfoxide (DMSO), KOH (2.3 g, 39.2 mmol) and 1-iodohexane (7.4 mL, 48.9 mmol) are added thereto, and the mixture is stirred at 75° C. for 2 hours. When the reaction is terminated, the resultant is purified through column chromatography.

[Reaction Scheme 2]

$^1$H-NMR (CDI$_3$, 300 MHz) d 8.37 (d, 2H), 8.31 (d, 2H), 8.19 (d, 2H), 7.58 (d, 2H), 7.52 (dd, 2H), 7.34 (t, 2H), 4.83 (t, 4H), 2.14 (m, 4H), 1.58 (m, 4H), 1.44 (m, 8H), 0.93 (t, 6H)

$^{13}$C-NMR (CDCl$_3$, 75 MHz) d 141.2, 136.5, 125.0, 123.1, 121.7, 119.8, 119.7, 118.9, 118.5, 114.3, 109.5, 46.8, 31.8, 30.5, 27.0, 22.8, 14.2

Example 3: Synthesis of Organic Semiconductor Compound (3)

The organic semiconductor compound (3) is synthesized according to Reaction Scheme 3. First, the organic semiconductor compound (1) of Example 1 (3 g, 9.8 mmol) is dissolved in 200 mL of dimethyl sulfoxide (DMSO), KOH (2.3 g, 39.2 mmol) and 1-iodooctane (9.0 mL, 48.9 mmol)

are added thereto, and the mixture is stirred at 75° C. for 2 hours. When the reaction is terminated, the resultant is purified through column chromatography.

[Reaction Scheme 3]

(1)

(3)

$^1$H-NMR (CDI$_3$, 300 MHz) d 8.39 (d, 2H), 8.31 (d, 2H), 8.19 (d, 2H), 7.58 (d, 2H), 7.52 (t, 2H), 7.50 (t, 2H), 4.83 (t, 4H), 2.15 (m, 4H), 1.58 (m, 4H), 1.43 (m, 4H), 1.34 (m, 12H), 0.98 (t, 6H)

$^{13}$C-NMR (CDCl$_3$, 75 MHz) d 141.3, 136.5, 125.1, 123.2, 121.8, 119.8, 119.7, 118.9, 118.4, 114.3, 109.5, 46.8, 32.0, 30.3, 29.6, 29.4, 27.3, 22.8, 14.3

Example 4: Synthesis of Organic Semiconductor Compound (4)

The organic semiconductor compound (4) is synthesized according to Reaction Scheme 4. First, the organic semiconductor compound (1) of Example 1 (3 g, 9.8 mmol) is dissolved in 200 mL of dimethyl sulfoxide (DMSO), KOH (2.3 g, 39.2 mmol) and 1-iododecane (12.3 mL, 48.9 mmol) are added thereto, and the mixture is stirred at 75° C. for 2 hours. When the reaction is terminated, the resultant is purified through column chromatography.

[Reaction Scheme 4]

(1)

(4)

$^1$H-NMR (CDI$_3$, 300 MHz) d 8.39 (d, 2H), 8.31 (d, 2H), 8.19 (d, 2H), 7.58 (d, 2H), 7.52 (dd, 2H), 7.33 (t, 2H), 4.84 (t, 4H), 2.15 (m, 4H), 1.57 (m, 6H), 1.43 (m, 4H), 1.29 (m, 22H), 0.88 (t, 6H)

$^{13}$C-NMR (CDCl$_3$, 75 MHz) d 141.2, 136.5, 125.0, 123.1, 121.7, 119.7, 118.9, 118.5, 114.4, 109.5, 46.8, 32.1, 30.4, 29.8, 29.6, 29.5, 27.3, 22.9, 14.3

Example 5: Synthesis of Organic Semiconductor Compound (5)

The organic semiconductor compound (5) is synthesized according to Reaction Scheme 5.

[Reaction Scheme 5]

(5-1)

(5)

1,5-diaminonaphthalene (1 g, 6.3 mmol) and 2-bromonaphthalene (2.9 g, 13.9 mmol) are dissolved in 200 mL of DMSO, Cu (18.9 mmol) is added thereto, and the mixture is refluxed and stirred at 150° C. When the reaction is terminated, the resultant is recrystallized, obtaining a desired organic semiconductor compound (5-1).

$^1$H-NMR (CDI$_3$, 300 MHz) d 7.88 (dd, 4H), 7.77 (dd, 4H), 7.56 (d, 2H), 7.50 (m, 4H), 7.37 (m, 4H), 6.96 (d, 2H), 4.0 (s, 2H)

$^{13}$C-NMR (CDCl$_3$, 75 MHz) d 142.6, 142.3, 133.7, 129.0, 126.8, 126.5, 126.3, 125.3, 124.6, 121.4, 118.1, 111.7, 109.0, 108.4

The organic semiconductor compound (5-1) (500 mg, 1.22 mmol), Pd(OAc)$_2$ (22 mg, 0.1 mmol), and Sn(OAc)$_2$ (60 mg, 0.1 mmol) are refluxed and stirred in 20 mL of AcOH. When the reaction is terminated, the resultant is recrystallized, obtaining a desired organic semiconductor compound (5).

$^1$H-NMR (CDI$_3$, 300 MHz) d 10.0 (s, 2H), 8.16 (m, 4H), 7.67 (dd, 4H), 7.57 (d, 2H), 7.55 (d, 2H), 7.40 (s, 2H)

$^{13}$C-NMR (CDCl$_3$, 75 MHz) d 144.2, 135.6, 133.5, 129.8, 127.3, 127.2, 120.5, 120.0, 118.8, 115.7, 144.2, 111.0

Example 6: Synthesis of Organic Semiconductor Compound (6)

The organic semiconductor compound (6) is synthesized according to Reaction Scheme 6. First, the organic semiconductor compound (5) of Example 5 (3 g, 7.4 mmol) is dissolved in 200 mL of dimethyl sulfoxide (DMSO), KOH (2.3 g, 39.2 mmol) and 1-iodohexane (5.6 mL, 36.9 mmol) are added thereto, and the mixture is stirred at 75° C. for 2 hours. When the reaction is terminated, the resultant is purified through column chromatography.

[Reaction Scheme 6]

(5)

(6)

$^1$H-NMR (CDI$_3$, 300 MHz) d 8.16 (m, 4H), 7.67 (dd, 4H), 7.57 (d, 2H), 7.55 (d, 2H), 7.40 (s, 2H), 4.83 (t, 4H), 2.14 (m, 4H), 1.58 (m, 4H), 1.44 (m, 8H), 0.93 (t, 6H)
$^{13}$C-NMR (CDCl$_3$, 75 MHz) d 144.2, 135.6, 133.5, 129.8, 127.3, 127.2, 120.5, 120.0, 118.8, 115.7, 144.2, 111.0, 46.8, 31.8, 30.5, 27.0, 22.8, 14.2

Example 7: Synthesis of Organic Semiconductor Compound (7)

The organic semiconductor compound (7) is synthesized according to Reaction Scheme 7. First, the organic semiconductor compound (5) of Example 5 (3 g, 7.4 mmol) is dissolved in 200 mL of dimethyl sulfoxide (DMSO), KOH (2.3 g, 39.2 mmol) and 1-iodooctane (6.8 mL, 36.9 mmol) are added thereto, and the mixture is stirred at 75° C. for 2 hours. When the reaction is terminated, the resultant is purified through column chromatography.

[Reaction Scheme 7]

(5)

(7)

$^1$H-NMR (CDI$_3$, 300 MHz) d 8.16 (m, 4H), 7.67 (dd, 4H), 7.57 (d, 2H), 7.55 (d, 2H), 7.40 (s, 2H), 4.83 (t, 4H), 2.15 (m, 4H), 1.58 (m, 4H), 1.43 (m, 4H), 1.34 (m, 12H), 0.98 (t, 6H)

$^{13}$C-NMR (CDCl$_3$, 75 MHz) d 144.2, 135.6, 133.5, 129.8, 127.3, 127.2, 120.5, 120.0, 118.8, 115.7, 144.2, 111.0, 46.8, 32.0, 30.3, 29.6, 29.4, 27.3, 22.8, 14.3

Example 8: Synthesis of Organic Semiconductor Compound (8)

The organic semiconductor compound (8) is synthesized according to Reaction Scheme 8. First of all, the organic semiconductor compound (5) of Example 5 (3 g, 7.4 mmol) is dissolved in 200 mL of dimethyl sulfoxide (DMSO), KOH (2.3 g, 39.2 mmol) and 1-iododecane (9.3 mL, 36.9 mmol) are added thereto, and the mixture is stirred at 75° C. for 2 hours. When the reaction is terminated, the resultant is purified through column chromatography.

[Reaction Scheme 8]

(5)

(8)

$^1$H-NMR (CDI$_3$, 300 MHz) d 8.16 (m, 4H), 7.67 (dd, 4H), 7.57 (d, 2H), 7.55 (d, 2H), 7.40 (s, 2H), 4.84 (t, 4H), 2.15 (m, 4H), 1.57 (m, 6H), 1.43 (m, 4H), 1.29 (m, 22H), 0.88 (t, 6H)
$^{13}$C-NMR (CDCl$_3$, 75 MHz) d 144.2, 135.6, 133.5, 129.8, 127.3, 127.2, 120.5, 120.0, 118.8, 115.7, 144.2, 111.0, 46.8, 32.1, 30.4, 29.8, 29.6, 29.5, 27.3, 22.9, 14.3

Example 9: Synthesis of Organic Semiconductor Compound (13)

A compound (13) is synthesized according to Reaction Scheme 9.

[Reaction Scheme 9]

13-5

In Reaction Scheme 9, R indicates a hexyl group.

2,6-dihydroxynaphthalene (5 g, 31.2 mmol), 1-iodohexane (23.5 mL, 156 mmol), and $K_2CO_3$ (21.6 g, 156 mmol) are refluxed and stirred with 500 mL of MeOH. When the reaction is complete, the resultant is purified through column chromatography, obtaining a compound (13-5).

$^1$H-NMR (CDI$_3$, 300 MHz) d 7.86 (d, 2H), 7.36 (d, 2H), 7.23 (d, 2H), 4.16 (t, 4H), 1.76 (m, 4H), 1.43 (m, 4H), 1.31 (m, 8H), 0.98 (s, 6H)

$^{13}$C-NMR (CDCl$_3$, 75 MHz) d 153.4, 130.5, 128.4, 117.8, 107.8, 46.8, 31.8, 30.5, 27.0, 22.8, 14.2

The compound (13-5) (5 g, 15.2 mmol) is dissolved in 150 mL of acetic acid (AcOH), Br$_2$ (9.7 g, 60.8 mmol) is slowly added thereto in a dropwise fashion, and the mixture is refluxed and stirred. When the reaction is complete, the resultant is recrystallized, obtaining compound (13-4).

$^1$H-NMR (CDI$_3$, 300 MHz) d 8.51 (s, 2H), 4.16 (t, 4H), 1.76 (m, 4H), 1.43 (m, 4H), 1.31 (m, 8H), 0.98 (s, 6H)

$^{13}$C-NMR (CDCl$_3$, 75 MHz) d 150.8, 129.0, 127.7, 118.6, 115.2, 46.8, 31.8, 30.5, 27.0, 22.8, 14.2

The compound (13-4) (5 g, 7.76 mmol) is dissolved in 50 mL of AcOH, Sn (1.85 g, 15.5 mmol) is slowly added thereto, and the mixture is refluxed and stirred. When the reaction is terminated, the resultant is recrystallized, obtaining a compound (13-3).

$^1$H-NMR (CDI$_3$, 300 MHz) d 7.99 (s, 2H), 7.28 (s, 2H), 4.16 (t, 4H), 1.76 (m, 4H), 1.43 (m, 4H), 1.31 (m, 8H), 0.98 (s, 6H)

$^{13}$C-NMR (CDCl$_3$, 75 MHz) d 152.0, 130.1, 129.2, 114.3, 106.0, 46.8, 31.8, 30.5, 27.0, 22.8, 14.2

The compound (13-3) (8.2 g, 16.8 mmol), bis(pinacolato)diboron (5.2 g, 20.1 mmol), PdCl$_2$(dppf)-CH$_2$Cl$_2$ (1.4 g, 1.68 mmol), and KOAc (5 g, 50.3 mmol) are added to 200 mL of dimethyl formamide (DMF), and the mixture is refluxed and stirred. When the reaction is terminated, the resultant is recrystallized, obtaining a compound (13-2).

$^1$H-NMR (CDI$_3$, 300 MHz) d 7.8 (s, 2H), 7.35 (s, 2H), 4.16 (t, 4H), 1.76 (m, 4H), 1.43 (m, 4H), 1.31 (m, 8H), 1.24 (s, 24H), 0.98 (s, 6H)

$^{13}$C-NMR (CDCl$_3$, 75 MHz) d 155.6, 130.5, 128.4, 105.6, 88.1, 69.0, 31.8, 29.6, 25.6, 24.7, 22.7, 14.1

The compound (13-2) (2 g, 3.45 mmol), 2-azido-3-bromonaphthalene (2.14 g, 8.63 mmol), Pd(PPh$_3$)$_4$ (350 mg, 0.3 mmol), and K$_2$CO$_3$ (2.6 g, 24.2 mmol) are added to 30 mL of toluene and 30 mL of H$_2$O, and the mixture is refluxed and stirred. When the reaction is terminated, the resultant is recrystallized, obtaining a desired compound (13-1).

$^1$H-NMR (CDI$_3$, 300 MHz) d 8.34 (s, 2H), 8.20 (s, 2H), 8.07 (s, 2H), 8.00 (dd, 4H), 7.59 (d, 4H), 7.42 (d, 2H), 4.16 (t, 4H), 1.76 (m, 4H), 1.43 (m, 4H), 1.31 (m, 8H), 0.98 (s, 6H)

$^{13}$C-NMR (CDCl$_3$, 75 MHz) d 154.4, 134.3, 133.1, 131.7, 129.9, 128.1, 127.5, 127.4, 126.4, 126.2, 124.1, 106.1, 69.0, 31.8, 29.6, 25.6, 22.7, 14.1

The compound (13-2) (2 g, 3.02 mmole) is dissolved in 200 mL of nitrobenzene, and the solution is refluxed and stirred. When the reaction is terminated, the resultant is recrystallized after removing a solvent therefrom, obtaining a desired organic semiconductor compound (13).

$^1$H-NMR (CDI$_3$, 300 MHz) d 10.1 (s. 2H), 8.16 (d, 4H), 7.67 (d, 4H), 7.45 (s, 2H), 7.40 (s, 2H), 6.93 (s, 2H), 4.16 (t, 4H), 1.76 (m, 4H), 1.43 (m, 4H), 1.31 (m, 8H), 0.98 (s, 6H)

$^{13}$C-NMR (CDCl$_3$, 75 MHz) d 150.5, 138.5, 135.5, 133.5, 130.2, 128.5, 127.3, 127.2, 126.5, 113.6, 111.0, 95.4, 69.0, 31.8, 29.6, 25.6, 22.7, 14.1

Figure 3:
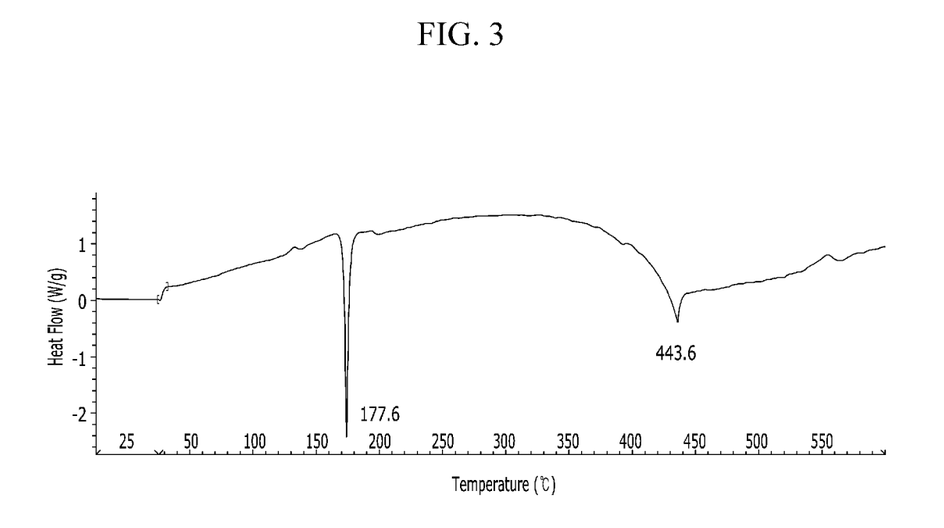
FIG. 3 shows a differential scanning calorimetry (DSC) analysis result of the organic semiconductor compound (2) according to Example 2.

Thermal stability of the organic semiconductor compounds according to Examples 1 to 9 is evaluated using a differential scanning calorimetry (DSC) analysis. FIG. 3 shows a differential scanning calorimetry (DSC) analysis result of the organic semiconductor compound (2) according to Example 2. Referring to FIG. 3, the organic semiconductor compound according to Example 2 has improved thermal stability.

Examples 10 to 19: Manufacture of Organic Thin Film Transistor (OTFT)

Firstly, chromium is deposited by sputtering to provide a 1000 Å-thick gate electrode of at on a cleaned glass substrate, and SiO$_2$ is deposited thereon by a CVD method to provide a 3000 Å-thick gate insulation layer. Then Au is deposited thereon by sputtering to provide a 700 Å-thick source electrode and a drain electrode. The glass substrate is washed for 10 minutes using isopropyl alcohol, and dried before coating the organic semiconductor compound.

The SiO$_2$ gate insulation layer is treated with UV/O$_3$ for 30 minutes. Then the resultant is dipped in an octyltrichloro silane solution that is diluted in n-hexane at a concentration of 10 mM for 30 minutes, and it is washed with hexane and alcohol and then dried. Each organic semiconductor compounds according to Examples 1 to 9 is dissolved in chlorobenzene to a concentration of 1.0 wt % and coated on the device by spin-coating, and then baked at 150° C. for one hour under a nitrogen atmosphere to provide an active layer. Thereby, it provides OTFT devices according to Examples 10 to 19 having a structure shown in FIG. 1.

Figure 4:
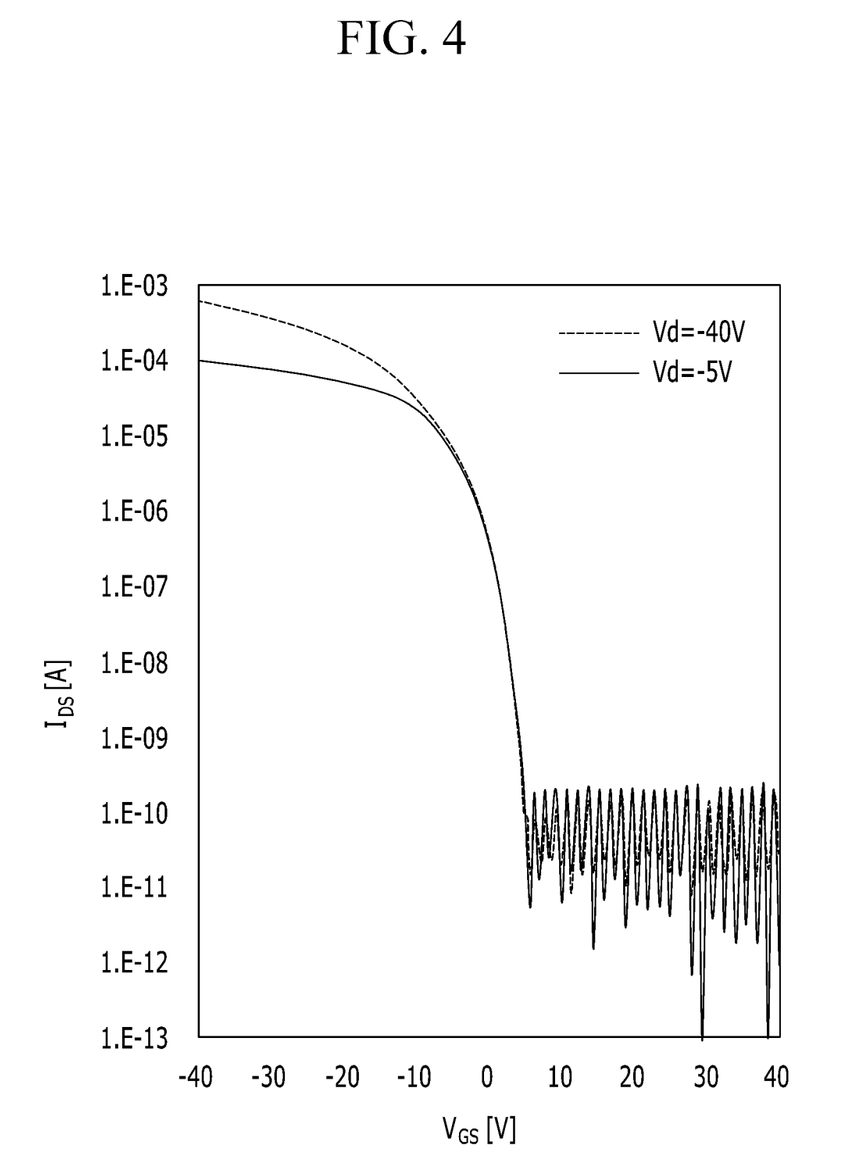
FIG. 4 shows a graph measuring current-transfer characteristics of the OTFT device including the organic semiconductor compound (2) according to Example 11.

The OTFT devices according to Examples 10 to 19 are measured for current-transfer characteristics using a semiconductor characterization system (4200-SCS, KEITHLEY CORP.). The result of the OTFT device according to Example 11 is shown in FIG. 4. As shown in FIG. 4, the OTFT device according to Example 11 shows improved charge mobility (9.2 cm$^2$/Vs).

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An organic semiconductor compound represented by Chemical Formula 1:

[Chemical Formula 1]

wherein, in Chemical Formula 1,
each of $R^1$ and $R^2$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, and a substituted or unsubstituted $C_2$ to $C_{30}$ alkynyl group,
each of $R^3$ to $R^8$ are independently one of hydrogen, a substituted or unsubstituted $C_1$ to $C_{10}$ alkyl group, and a substituted or unsubstituted $C_1$ to $C_{10}$ alkoxy group,
each of n1 and n2 are independently one of 0 to 2,
m is 1,
each of a and f are independently one of 0 to 4, and
each of b, c, d, and e are independently one of 0 to 2.

2. The organic semiconductor compound of claim 1, wherein the $R^1$ and $R^2$ groups are one of a substituted or unsubstituted $C_{10}$ to $C_{30}$ alkyl group, a substituted or unsubstituted $C_{10}$ to $C_{30}$ alkoxy group, a substituted or unsubstituted $C_{10}$ to $C_{30}$ alkenyl group, and a substituted or unsubstituted $C_{10}$ to $C_{30}$ alkynyl group.

3. The organic semiconductor compound of claim 1, wherein the $R^1$ and $R^2$ groups are a fluoro substituted $C_1$ to $C_{30}$ alkyl group.

4. The organic semiconductor compound of claim 1, wherein the $R^1$ and $R^2$ groups are a $C_1$ to $C_{30}$ perfluoro alkyl group.

5. The organic semiconductor compound of claim 1, wherein the organic semiconductor compound is represented by one of Chemical Formulae 1A to 1B and 1D to 1E:

[Chemical Formula 1A]

[Chemical Formula 1B]

[Chemical Formula 1D]

[Chemical Formula 1E]

wherein, in the Chemical Formulae 1A to 1B and 1D to 1E,
each of $R^1$ and $R^2$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, and a substituted or unsubstituted $C_2$ to $C_{30}$ alkynyl group,
each of $R^3$ to $R^8$ are independently one of hydrogen, a substituted or unsubstituted $C_1$ to $C_{10}$ alkyl group, and a substituted or unsubstituted $C_1$ to $C_{10}$ alkoxy group,
each of a and f are independently one of 0 to 4, and
each of b, c, d, and e are independently one of 0 to 2.

6. The organic semiconductor compound of claim 1, wherein the organic semiconductor compound has an average molecular weight of 350 to 3,000.

7. An organic thin film comprising the organic semiconductor compound of claim 1.

8. An electronic device comprising the organic semiconductor compound of claim 1.

9. The electronic device of claim 8, wherein the electronic device is one of a transistor, an organic light emitting diode (OLED), a photovoltaic device, a solar cell, a laser device, a memory device, and a sensor.

10. The electronic device of claim 8, wherein:
the electronic device includes at least one charge transport layer; and
the organic semiconductor compound is included in the charge transport layer.

* * * * *